(12) United States Patent
Slishman

(10) Patent No.: US 6,394,972 B1
(45) Date of Patent: May 28, 2002

(54) TRACTION SPLINT

(75) Inventor: Samuel Slishman, Albuquerque, NM (US)

(73) Assignee: Science and Technology Corporation @ UNM, Albuquerque, NM (US)

(*) Notice: Subject to any disclaimer, the term of this patent is extended or adjusted under 35 U.S.C. 154(b) by 0 days.

(21) Appl. No.: 09/450,434

(22) Filed: Nov. 30, 1999

(51) Int. Cl.⁷ .................................................. A61F 5/00
(52) U.S. Cl. .................................. 602/32; 62/36; 62/38
(58) Field of Search ............................... 602/5, 20, 23, 602/32–36, 38; 128/878, 882, 845–846; 606/237, 241–244; 248/125.8, 157, 125.2, 188.2–188.3; 182/200, 201, 202, 204

(56) References Cited

U.S. PATENT DOCUMENTS

| | | |
|---|---|---|
| 82,478 A | 9/1868 | Ballard |
| 350,526 A | 10/1886 | Bunce |
| 2,058,563 A * | 10/1936 | Campbell ................... 128/25 |
| 2,186,456 A * | 1/1940 | Gordon ....................... 602/20 |
| 2,252,258 A | 8/1941 | Hayden |
| 2,260,216 A | 10/1941 | Doyle |
| 2,394,653 A | 2/1946 | Auerhaan |
| 3,299,888 A | 1/1967 | Muckinhaupt |
| 3,413,971 A * | 12/1968 | Evans .......................... 602/33 |
| 3,454,002 A | 7/1969 | Westlake et al. |
| 3,503,390 A * | 3/1970 | Peters ......................... 602/33 |
| 3,750,659 A | 8/1973 | Loomans |
| 3,756,227 A * | 9/1973 | Sager .......................... 128/85 |
| 3,888,243 A * | 6/1975 | Powlan ........................ 128/75 |
| 3,942,521 A | 3/1976 | Klippel |
| 4,608,971 A * | 9/1986 | Borschneck ................. 128/85 |
| 4,649,907 A | 3/1987 | Whitehead et al. |
| 4,911,152 A | 3/1990 | Barnes et al. |
| 5,019,077 A | 5/1991 | De Bastiani et al. |
| 5,181,094 A * | 1/1993 | Cook et al. .................... 602/32 |
| 5,230,700 A | 7/1993 | Humbert et al. |
| 5,342,288 A | 8/1994 | Lee et al. |
| 5,775,334 A * | 7/1998 | Lamb et al. ................. 128/845 |
| 5,778,914 A * | 7/1998 | Trani .......................... 135/66 |

\* cited by examiner

*Primary Examiner*—Denise Pothier
(74) *Attorney, Agent, or Firm*—Jagtiani + Guttag

(57) ABSTRACT

The present invention provides a splint that may be telescopically extendable, coarsely and finely adjustable, and providing a mechanical advantage while being readily transportable. The splint may have two to three telescoping members that nest inside one another when not in use, and may be triangular, rectangular, or circular in cross section. The present invention also provides a single member adjustable splint.

16 Claims, 9 Drawing Sheets

TRACTION SPLINT

BACKGROUND OF THE INVENTION

1. Field of the Invention

The present invention relates generally to traction splints.

2. Description of the Prior Art

There have been several attempts to design portable devices that provide external traction to an injured limb. For example, U.S. Pat. No. 4,608,971 to Borschneck describes an emergency leg splint that telescopes for length adjustment. However, splints like Borschneck's are relatively large and heavy making them difficult to transport.

Splints designed to be portable such as Borschneck's also do not provide a mechanical advantage, so these splints cannot be used to reduce fractures or relocate joints like the elbow, shoulder, knee or hip. Current portable splints are also generally designed specifically to immobilize a person's leg or specifically to immobilize a person's arm, so it is necessary to have available both a leg splint and an arm splint to select from depending on the limb injured. Furthermore, current portable splints cannot be adjusted to exactly fit the limb being supported.

SUMMARY OF THE INVENTION

It is therefore an object of the present invention to provide a compact, lightweight versatile splint.

It is another object of the present invention to provide a splint having both a coarse and a fine adjustment device.

It is another object to provide a splint having a mechanical advantage.

In a first aspect, the present invention provides a splint comprising: an outer member having a distal end and a proximal end; a middle member slidable in a longitudinal direction within the outer member, the middle member having a distal end and a proximal end; an inner member slidable in a longitudinal direction within the middle member, the inner member having a distal end and a proximal end; a coarse adjustment means for adjusting a distance between the distal end of the middle member and a proximal end of the outer member by a plurality of course increments; a fine adjustment means for adjusting a distance between the distal end of the inner member and a proximal end of the middle member by a plurality of fine increments.

In a second aspect, the present invention provides a splint comprising: an outer member having a distal end and a proximal end; an inner member slidable in a longitudinal direction within the outer member, the inner member having a distal end and a proximal end; an adjustment means for adjusting a distance between the distal end of the inner member and a proximal end of the outer member by a plurality of fine increments.

In a third aspect, the present invention provides a splint comprising: an elongated member having a distal end and a proximal end; a cord means extending through a hollow portion of the elongated member, the cord means including: a distal securing means for securing the elongated member to a limb of an individual, the distal securing means mounted at one end to the distal end of the elongated member and a loop portion extending from the distal end of the elongated member; a free end for grasping by a user and for allowing a user to pull on the cord means to cause the loop portion of the distal securing means to pull the limb of the individual towards the elongated member; and a connecting portion connecting the loop portion of the distal securing means to the free end; and a proximal securing means for securing the elongated member to the limb of the individual, the proximal securing means being mounted on the elongated member at a position proximal to the distal end of the elongated member.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Definitions

Figure 1A:
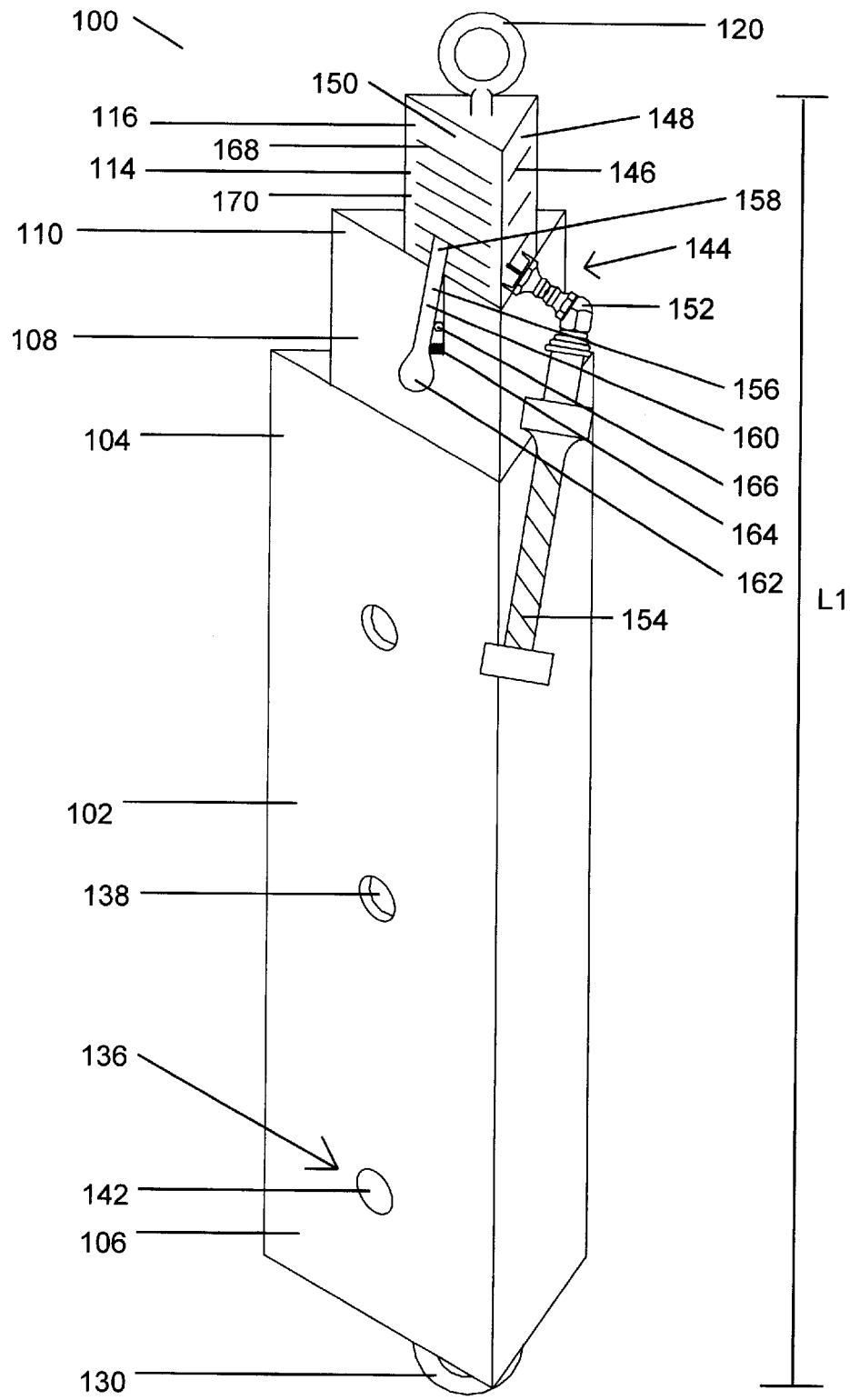
FIG. 1A is a schematic perspective view of a first embodiment of a traction splint of the present invention.

For the purposes of the present invention the term "individual" refers to either an individual person or animal on whom the splint of the present invention is used.

Unless specified or shown otherwise, for the purposes of the present invention, the term "distal end" generally refers to the end of a splint from which an inner member of the splint extends or from which an adjustable securing device extends. The other end of the splint is referred to as the "proximal end".

For the purposes of the present invention, the term "longitudinal" refers to a direction along the length of a splint from either the proximal end to distal end or from the distal end to the proximal end.

For the purposes of the present invention, the term "opposed openings" refers to a pair of corresponding openings on opposite sides of a member.

For the purposes of the present invention, the term "cord" refers to any type of cord, natural or synthetic rope, line, chain, etc. that can be used with a pulley of the present invention. When used as part of an adjustment device of the present invention, the cord is preferably flexible yet sufficiently strong to resist tearing or breaking while passing over pulley posts and moving inner and middle members relative to one another. Although the term a rope is used as a cord in the embodiments shown in the drawing figures and described below, it should be understand that various kinds of cords can be used in place of the rope of these embodiments.

For the purposes of the present invention, the term "pulley" refers to one or more surfaces, one or more posts, one or more wheels, etc. over which, around which, or through which a cord of the present invention travels to provide a user of a traction splint of the present invention with a mechanical advantage. For the purposes of the present invention, the term "pulley system" refers to the combination of the cord and all of the pulleys in a particular traction splint of the present invention. Utilizing multiple wheels as pulleys in a pulley system of the present invention allows the user to increase the mechanical advantage of a traction splint of the present invention.

For the purposes of the present invention, the term "limb" refers to any part of a person's leg, including: the foot, ankle, knee, hip, etc. and any part of a person's arm, including: the shoulder, elbow, wrist, hand, etc. The term "limb" may also refer to any part of an individual which may be braced by a rod or splint such as an individual's back, neck, etc.

For the purposes of the present invention, the phrase "securing a splint to a limb" refers not only to directly securing the splint of the present invention to an individual's limb, but also to securing the splint clothing or other objects adjacent to, surrounding or attached to an individual's limb. For example, the splint of the present invention may be secured to an individual's sleeve, pant's leg, sock, shoe, thigh pad, leg wrap, etc.

For the purposes of the present invention, the term "analog adjustment device" refers to a device that may increase or decrease the length of the splint of the present invention by a wide variety of different increments. For example, the pulley system illustrated in the embodiment of FIG. 3A below is such an analog adjustment device. The pulley system allows the length of the splint to be extended by very small, almost continuous increments. In contrast, the term "discrete adjustment device" refers to devices which adjust the length of the splint of the present invention by particular set amounts. For example, both adjustment devices described in the embodiment illustrated in FIG. 1A are "discrete adjustment devices". In these two adjustment devices, the spacing of the holes or slots determines the increments by which the splint's length may be extended.

For the purposes of the present invention, the terms "coarse adjustment" and "fine adjustment" are relative. For a particular splint of the present invention, a coarse adjustment device adjusts the length of a splint by an increment larger than the increment that the fine adjustment device adjusts the length of the splint.

Figure 1B:
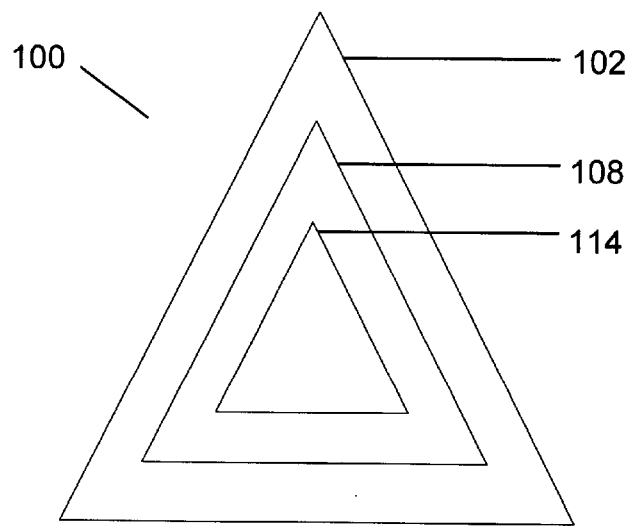
FIG. 1B is a schematic cross-sectional view of the embodiment of FIG. 1A.
Figure 1C:
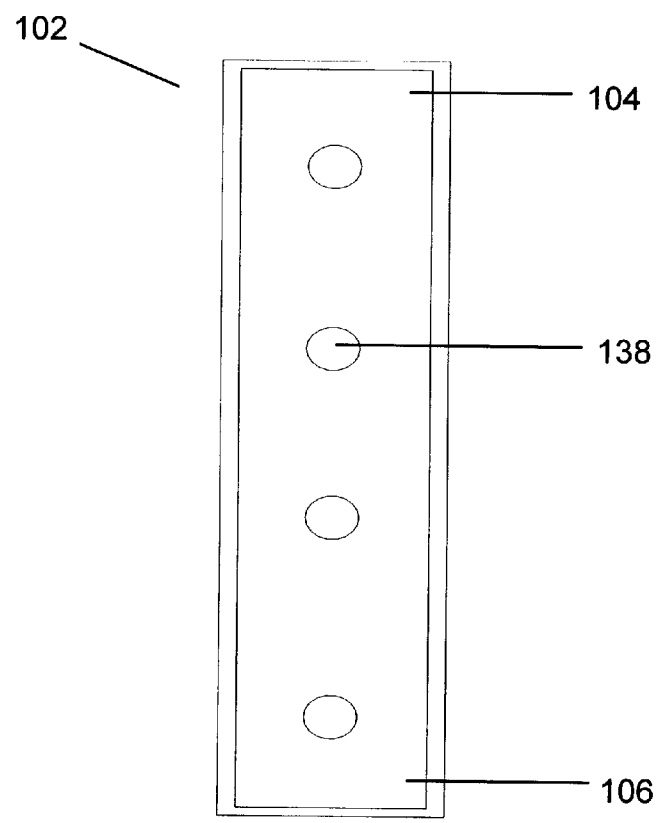
FIG. 1C is a schematic perspective view of an outer member of the embodiment of FIG. 1A.

For the purposes of the present invention, the term "selectively engaging" refers to a plunger, rod, etc. extending into or through one or more openings that are aligned with the plunger, rod, etc. when two or more of the members of the splint of the present invention are in given relationship with one another. For example, in a splint such as that shown in FIGS. 1A and 1B, a plunger on the middle member may selectively engage the first, second, or third opening from the distal end of the outer member, depending on the position of the outer member relative to the middle member.

For the purposes of the present invention, the term "attached" when referring to a cord of the present invention being attached to member of a splint of the present invention refers to a variety of conventional methods of attachment of one end of a cord to a member. For example, when the cord of the present invention is a rope, a rope can be attached to member threading one end of a rope through a hole in the member and knotting the rope so that the end of the rope cannot pass back through the hole. A rope can also be attached with an adhesive, cleat, velcro, staple, etc. or other conventional means for fixing a rope to a member. What is important is that when a cord of the present invention is attached to a member, the attached end of the cord is held or eventually prevented from moving any further, such as by a knot being prevented from going through a hole, when a user pulls on the free end of the cord.

For the purposes of the present invention, the term "constriction loop" refers to an adjustable loop that is used to secure a member of a splint of the present invention to a limb of an individual. A constriction loop is adjustable in the sense that the diameter of a constriction loop can be adjusted to fit the diameter of one of the portions of the limb to which the traction splint of the present invention is secured. A constriction loop can be formed by twisting an adjustable cord of the present invention or may be a separate loop mounted on an adjustable cord of the present invention. A constriction loop may be constructed from rope, velcro, cloth, etc.

Description

FIGS. 1A, 1B, 1C, 1D, and 1E illustrate one preferred embodiment of the present invention. A three-member traction splint 100 includes an outer member 102 having an outer member distal end 104 and an outer member proximal end 106. Located inside outer member 102 is a middle member 108 having a middle member distal end 110 and a middle member proximal end 112 (visible in FIG. 1D). Located inside middle member 108 is an inner member 114 having an inner member distal end 116 and an inner member proximal end 118 (visible in FIG. 1E). A distal securing device 120 is provided at inner member distal end 116, and a proximal securing device 130 is provided at outer member proximal end 106. Distal securing device 120 and proximal securing device 130 allow traction splint 100 to be secured to an individual (not shown).

In the embodiment shown in FIGS. 1A through 1E, the distal securing device and the proximal securing device are shown as rings that could receive a rope, hook and loop fastener, or any other appropriate means of attaching the splint of the present invention to the individual. The distal securing device and the proximal securing device can be fixed or removably attached, and can be of any variety of sizes and shapes as desired for a particular use. While the members shown in the embodiment of FIGS. 1A through 1E are triangular in cross-section, it is contemplated that the members could be circular, oval, square, rectangular, or other shape in cross-section.

Traction splint 100 includes a coarse adjustment device 136. Coarse adjustment device 136 consists of a series of circular holes 138 and a conventional spring loaded plunger 142 (only a portion of which is visible in FIG. 1A). Although there are three holes depicted, the number can vary depending on the particular use. Spring loaded plunger 142 is mounted on middle member 108 and is designed to engage any one of holes 138. Only one of holes 138 may be engaged at any time, and plunger 142 must be actively depressed to disengage plunger 142 from one of holes 138. Once plunger 142 is disengaged, middle member 108 and plunger 142 can be moved along the inside of outer member 102 until desired one of holes 138 is engaged as shown in FIG. 1A. Using the procedure just described, coarse adjustment device 136 is able to fix the location of middle member 108 relative to outer member 102 and provides coarse adjustment of splint length $L_1$.

Although the holes and corresponding plunger of the coarse adjustment device are depicted as circular in the embodiment shown in FIGS. 1A through 1E, other shapes such as oval, triangular, square, etc. may be used in the traction splint of the present invention. Also, the coarse adjustment device may consist of a pair of opposing holes through which a screw, bolt, etc. may extend to fix the position of the middle member relative to the outer member.

Figure 1D:
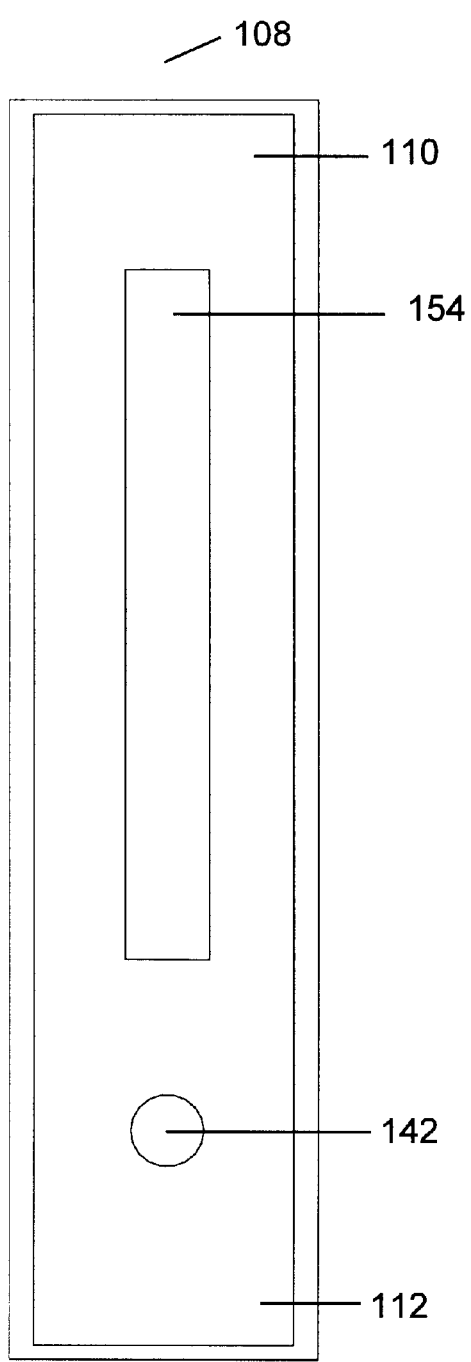
FIG. 1D is a schematic side view of a middle member of the embodiment of FIG. 1A.
Figure 1E:
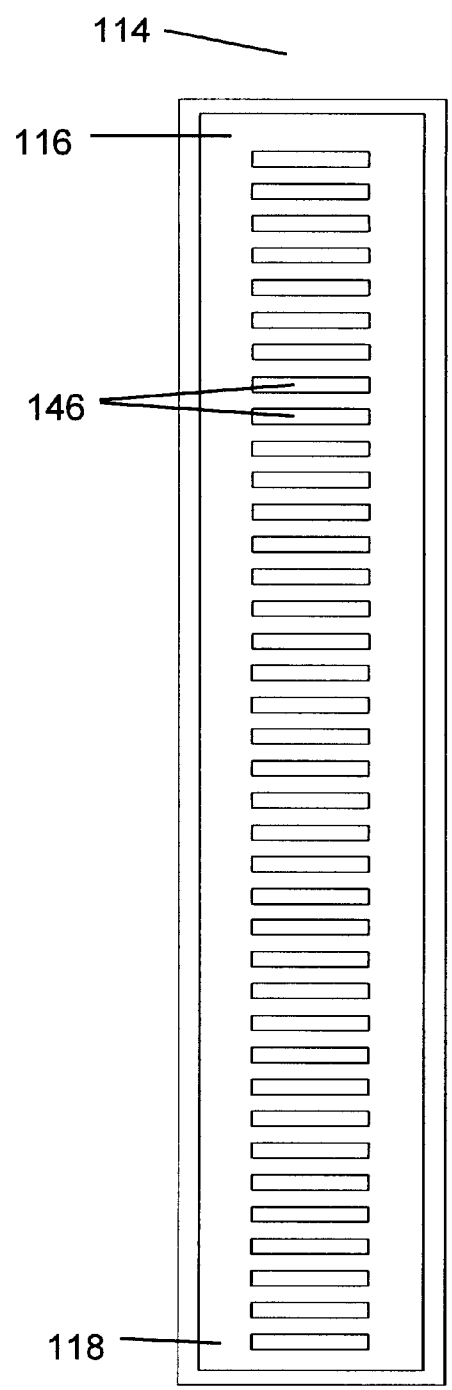
FIG. 1E is a schematic side view of an inner member of the embodiment of FIG. 1A.

Traction splint 100 also includes a fine adjustment device 144. Fine adjustment device 144 consists of a plurality of slots or openings 146 on an inner member first side 148 that are engaged by a ratchet 152. A ratchet handle 154 allows a user (not shown) to manipulate ratchet 152. When not in use, ratchet handle 154 is stored on middle member 108 as depicted in FIG. 1D. A brake 156 for fine adjustment device 144 consists of a brake distal end 158, a brake middle portion 160, a brake proximal end 162, a spring or brake resistance device 164, and a brake pivot 166. Brake proximal end 162 can be depressed by a user (not shown) to disengage brake 156. Brake distal end 158 is configured to engage openings 168 on a second side 170 of inner member 150. Brake distal end 158 is urged against second side of inner member 150 by brake resistance device 164 located between brake proximal end 162 and middle member distal end 110. Inner member distal end 116 is free to move in a distal direction away from middle member distal end 110 when brake 156 is in use. However, openings 168 will engage brake distal end 158 and thereby stop inner member distal end 116 as inner member distal end 116 travels toward middle member distal end 110. Brake pivot 166 is located between brake 156 and middle member 108. Brake pivot 166 allows the use of brake resistance device 164 to urge brake distal end 158 to engage inner member 114.

Fine adjustment device 144 restrains the movement of middle member 108 relative to inner member 114 and provides fine adjustment of splint length $L_1$.

The ratchet, brake, and slots of the fine adjustment device of the present invention can vary in size and distribution to change the degree of fine adjustment of the traction splint of the present invention.

The combination of coarse and fine adjustments shown in the embodiment of FIGS. 1A through 1E allow the splint to apply precise and tight traction and may be used to reduce fractures or dislocated joints. Furthermore, the compact design allows the splint to be portable. Such a portable splint can be used by backpackers as well as all types of emergency medical personnel. The traction splint of the present invention can also be utilized for injuries to the upper and lower extremities.

Figure 2A:
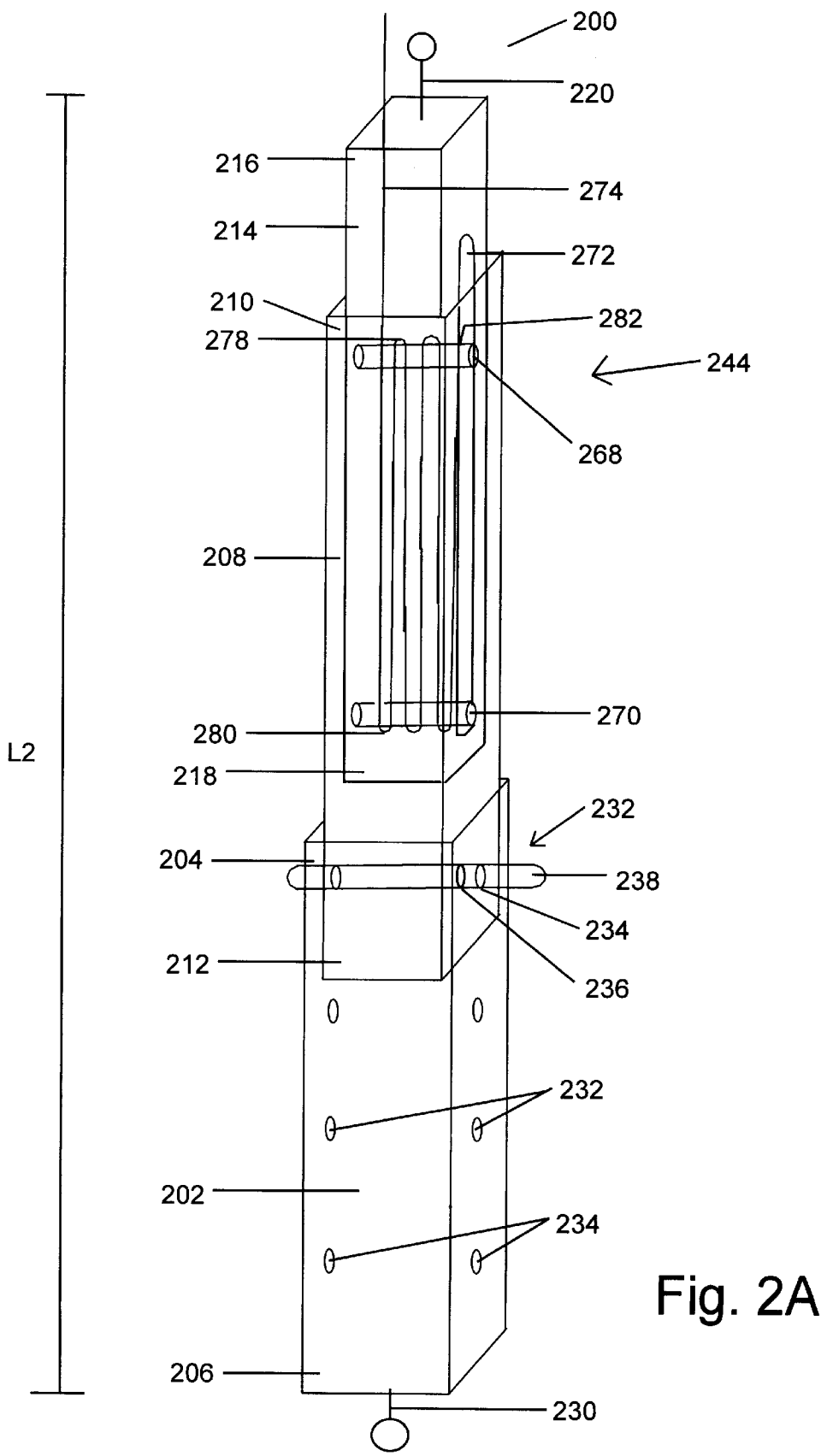
FIG. 2A is a schematic perspective view of a second embodiment of a traction splint of the present invention.
Figure 2B:
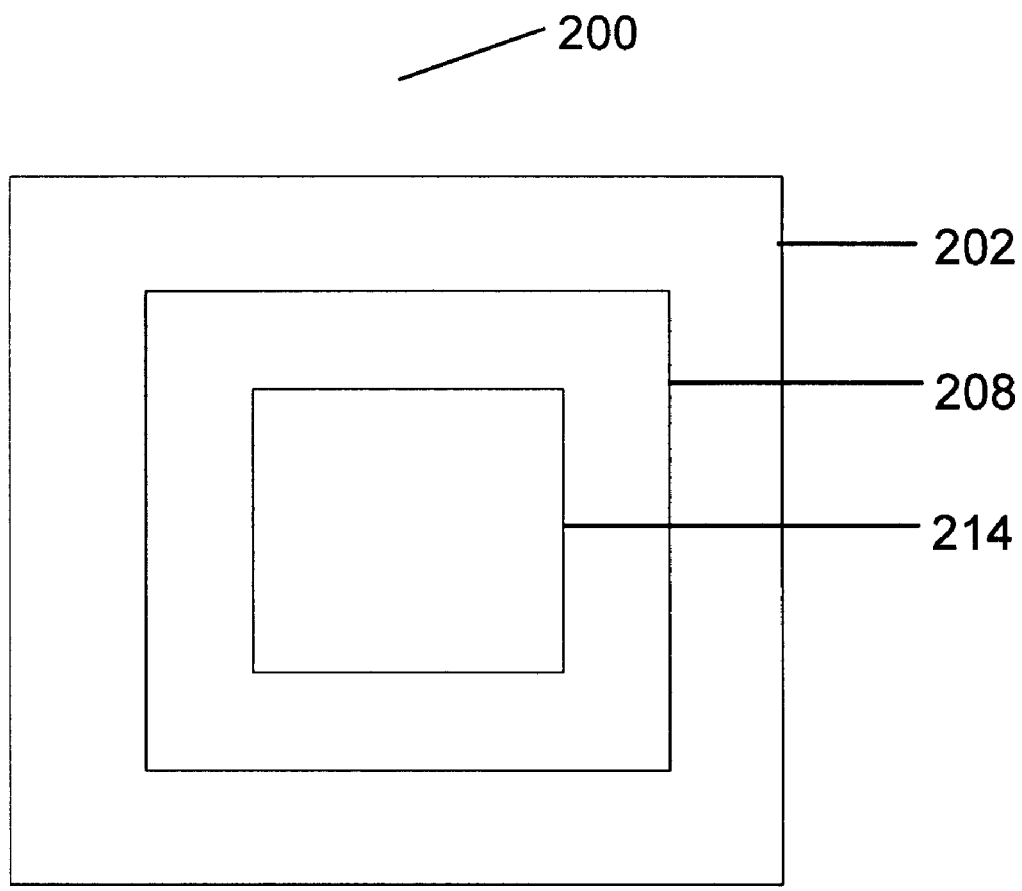
FIG. 2B is a schematic cross-sectional view of the embodiment of FIG. 2A.

FIGS. 2A and 2B illustrate a second preferred embodiment of the present invention. A three-member traction splint 200 includes an outer member 202 having an outer member distal end 204 and an outer member proximal end 206. Located inside outer member 202 is a middle member 208 having a middle member distal end 210 and a middle member proximal end 212. Located inside middle member 208 is an inner member 214 having an inner member distal end 216 and an inner member proximal end 218. A distal securing device 220 is provided at inner member distal end 216, and a proximal securing device 230 is provided at outer member proximal end 206. Distal securing device 220 and proximal securing device 230 allow traction splint 200 to be secured to an individual (not shown).

Although for convenience the members of the traction splint shown in FIGS. 2A and 2B are made of a translucent or transparent plastic material, the materials used to form the traction splint of the present invention may be solid materials as shown in the embodiment of FIGS. 1A through 1E.

In the embodiment shown in FIGS. 2A and 2B, the distal securing device and the proximal securing device are shown as rings that can receive a rope, hook and loop fastener, or any other appropriate means of attaching the splint of the present invention to the individual. The distal securing device and the proximal securing device can be fixed or removably attached, and can be of any variety of sizes and shapes as desired for a particular use.

While the members shown in the embodiment of FIGS. 2A and 2B are square in cross-section, it is contemplated that the members of the traction splint of the present invention can be circular, oval, triangular, rectangular, or other shape in cross-section.

Traction splint 200 includes a coarse adjustment device 232. Coarse adjustment device 232 consists of a series of pairs of longitudinally aligned holes 234 in outer member 202, a pair of opposed holes 236 in middle member 208, and a removable locking post 238 which is inserted through holes 236 and a selected pair of holes 234 to fix the position of middle member 208 relative to outer member 202, thereby providing coarse adjustment of splint length $L_2$.

Although the holes and removable locking post of the coarse adjustment device are depicted as circular, other shapes such as oval, triangular, square, etc. may be used in the traction splint of the present invention. Also, the locking post can be replaced with a nail, screw, etc. A flattened end on one or both ends of locking post may be desirable to maintain locking post in a fixed position once the desired series of holes are engaged.

A fine adjustment device 244 is also provided for traction splint 200. Fine adjustment device 244 is comprised of a distal pulley post 268, a proximal pulley post 270, a pair of openings or slots 272 in inner member 214, and a rope 274. Proximal pulley post 270 is mounted to the inside of inner member 214, and distal pulley post 268 is mounted to the inside of middle member 208. Loops 278 and 280 of rope wrap around distal pulley post 268 and proximal pulley post 270, respectively. Openings 272 in inner member 214 allow for movement of inner member 214 relative to middle member 208 without inner member 214 contacting distal pulley post 268. A user of traction splint 200 can pull on the free end of rope 274 to cause loops 278 and 280 of rope 274 around distal pulley post 268 and proximal pulley post 270, respectively, to tighten and pull distal pulley post 268 and proximal pulley post 270 toward one another. Fine adjustment device 244 allows for movement of inner member 214 relative to middle member 208 and provides fine adjustment of splint length l. Fine adjustment device 244 also provides mechanical advantage. That allows splint to reduce fractures or dislocations without requiring great strength or exertion by the user.

The non-free end of the rope used to finely adjust the traction splint of the present invention may be secured to either pulley post, to either inner or middle member, or to any other suitable location on the splint.

Figure 3A:
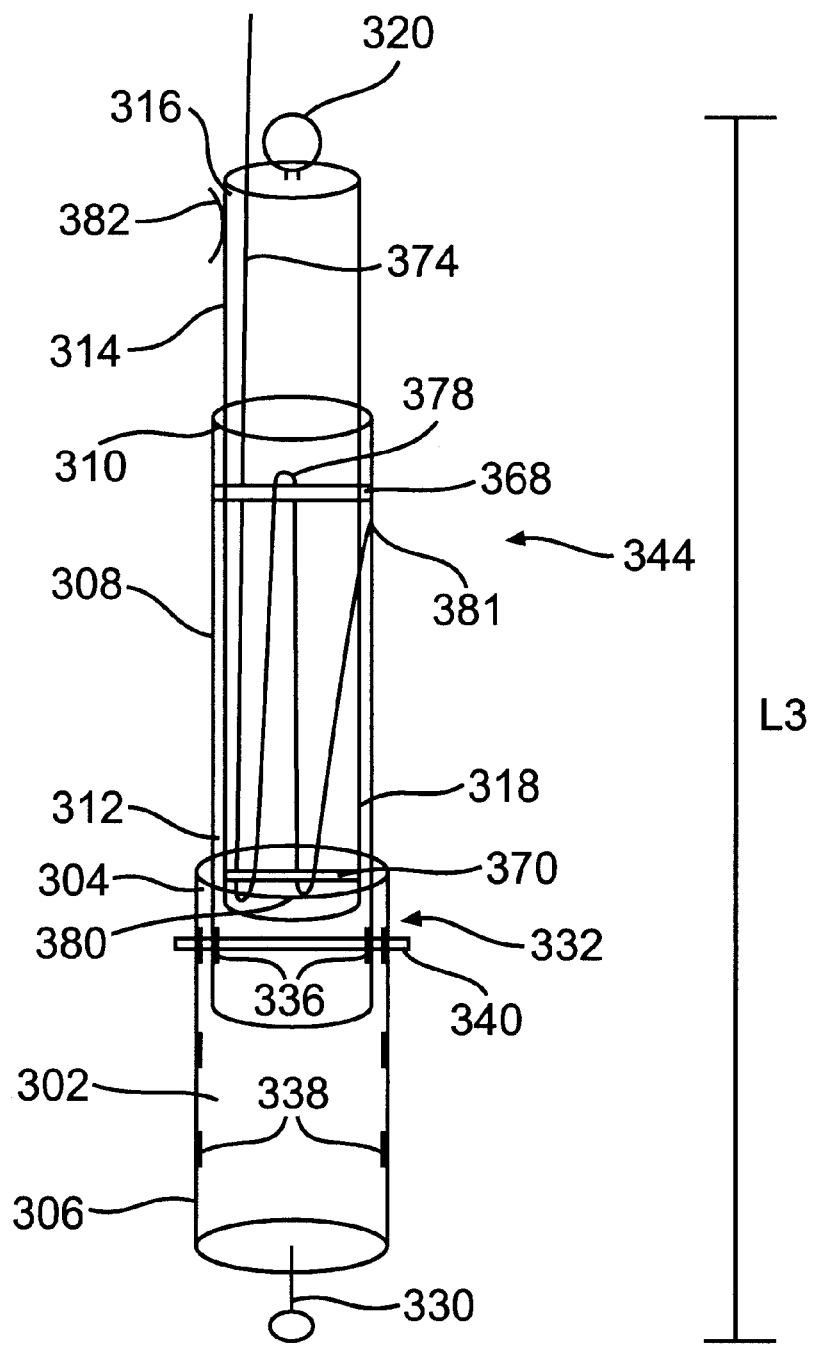
FIG. 3A is a schematic perspective view of a third embodiment of a traction splint of the present invention.
Figure 3B:
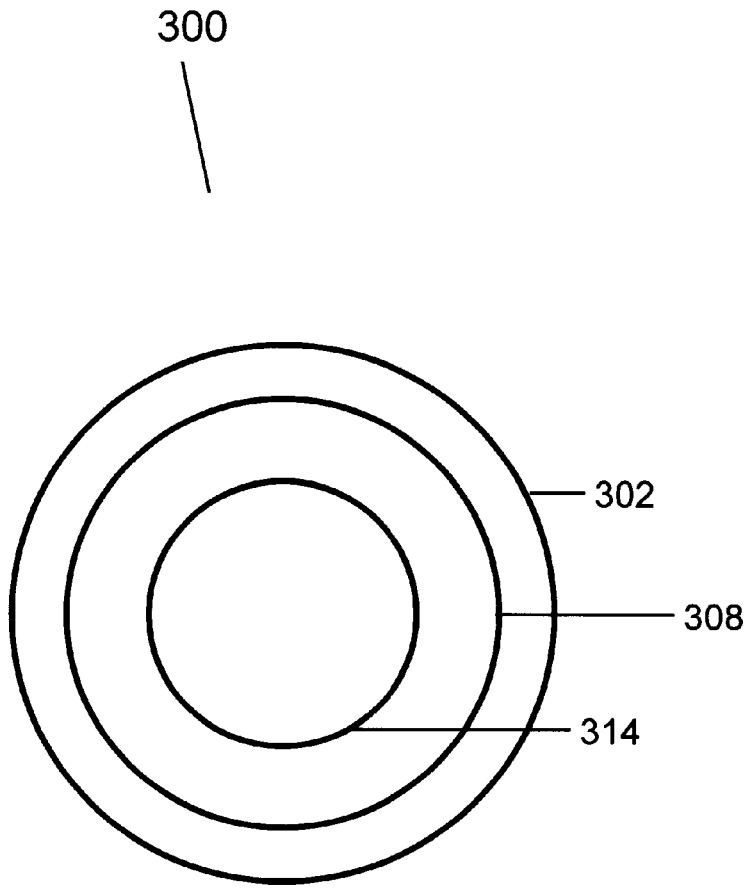
FIG. 3B is a schematic cross-sectional view of the embodiment of FIG. 3A.

FIGS. 3A and 3B illustrate a third preferred embodiment of the present invention. A three-member traction splint 300 includes an outer member 302 having an outer member distal end 304 and an outer member proximal end 306.

Located inside outer member 302 is a middle member 308 having a middle member distal end 310 and a middle member proximal end 312. Located inside middle member 308 is an inner member 314 having an inner member distal end 316 and an inner member proximal end 318. A distal securing device 320 is provided at inner member distal end 316, and a proximal securing device 330 is provided at outer member proximal end 306. Distal securing device 320 and proximal securing device 330 allow traction splint 300 to be secured to an individual (not shown).

In the embodiment shown in FIGS. 3A and 3B, the distal securing device and the proximal securing device are shown as rings that can receive a rope, hook and loop fastener, or any other appropriate means of attaching the splint of the present invention to an individual. The distal securing device and the proximal securing device can be fixed or removably attached, and can be of any variety of sizes and shapes as desired for a particular use. While the members of the traction splint shown in the embodiment of FIGS. 3A and 3B are circular in cross-section, it is contemplated that the members can be, oval, triangular, square, rectangular, or other shape in cross-section.

Traction splint 300 includes a coarse adjustment device 332. Coarse adjustment device 332 consists of a series of pairs of longitudinally aligned holes 338 in outer member 302, a pair of opposed holes 336 in middle member 308, and a removable locking post 340 which is inserted through holes 336 and a selected pair of holes 338 to fix the position of middle member 308 relative to outer member 302, thereby providing coarse adjustment of splint length $L_3$.

Although the holes and removable locking post of the coarse adjustment device are depicted as circular, other shapes such as oval, triangular, square, etc. may be used in the traction splint of the present invention. Also, the locking post can be replaced with a nail, screw, etc. A flattened end on one or both ends of the locking post may be desirable to maintain the locking post in a fixed position once the desired series of holes is engaged.

A fine adjustment device 344 is also provided for traction splint 300. Fine adjustment device 344 is comprised of a distal pulley post 368, a proximal pulley post 370, and a rope 374. Proximal pulley post 370 is mounted to the inside of inner member 314, and distal pulley post 368 is mounted to the inside of middle member 308. Loops 378 and 380 of rope 374 wrap around distal pulley post 368 and proximal pulley post 370, respectively. Openings in inner member 314 (not shown) allow for movement of inner member 314 relative to middle member 308 without inner member 314 contacting distal pulley post 368. A user of traction splint 300 can pull on the free end of rope to cause loops 378 and 380 of rope 374 around distal pulley post 368 and proximal pulley post 370, respectively, to tighten and pull distal pulley post 368 and proximal pulley post 370 toward one another. Fine adjustment device 344 allows for movement of inner member 314 relative to middle member 308 and provides fine adjustment of splint length $L_3$. Fine adjustment device 344 also provides mechanical advantage. That allows splint to reduce fractures or dislocations without requiring great strength or exertion by the user. Rope 374 is attached to middle member distal end 310 at a rope attachment point 381. Once a desired splint length $L_3$ is achieved, free end of rope can be secured at a cleat 382. Fine adjustment device 344 allows inner member 314 to be moved relative to middle member 308 and allows fine adjustment of splint length $L_3$.

The fine adjustment device of the traction splint of FIGS. 3A and 3B provides mechanical advantage. Mechanical advantage allows the splint to reduce fractures or dislocations without great strength or exertion by the user. The cleat is shown at the inner member distal end, but other locations on or in the splint may be utilized. The cleat may be a conventional cleat, a hook, or other suitable fastener for securing the rope.

Figures 4A, 4B:
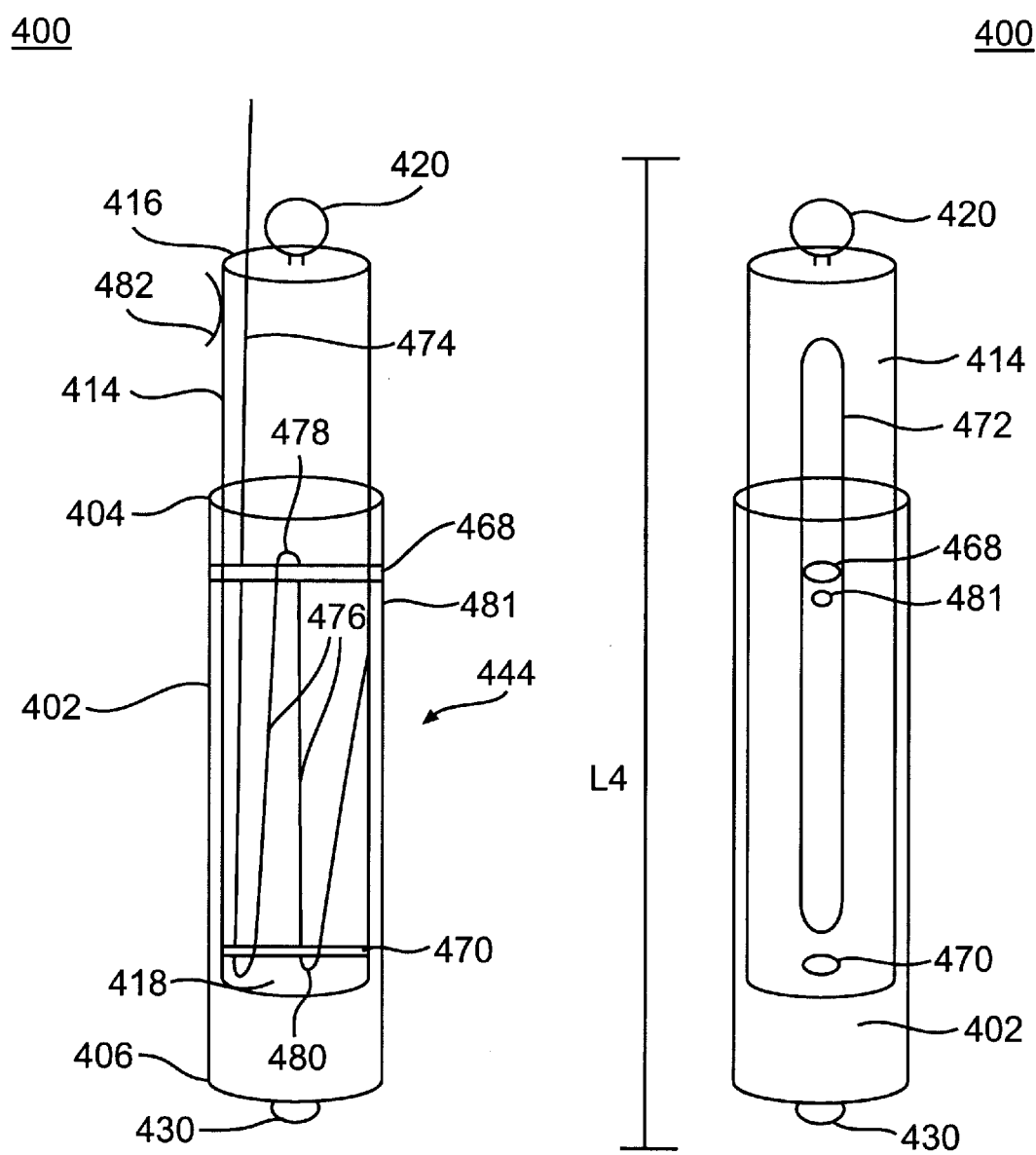
FIG. 4A is a schematic perspective view from one angle of a fourth embodiment of a traction splint of the present invention.
FIG. 4B is a schematic perspective view from a second angle of the embodiment of FIG. 4A.

FIGS. 4A and 4B illustrate a fourth preferred embodiment of the present invention. A two-member traction splint 400 includes an outer member 402 having an outer member distal end 404 and an outer member proximal end 406. Located inside outer member 402 is an inner member 414 having an inner member distal end 416 and an inner member proximal end 418. A distal securing device 420 is provided at inner member distal end 416, and a proximal securing device 430 is provided at outer member proximal end 406. Distal securing device 420 and proximal securing device 430 attach splint 400 to an individual (not shown).

In the embodiment shown in FIGS. 4A and 4B, the distal securing device and the proximal securing device are shown as rings that can receive a rope, hook and loop fastener, or any other appropriate means of attaching the splint of the present invention to the individual. The distal securing device and the proximal securing device can be fixed or removably attached, and can be of any variety of sizes and shapes as desired for a particular use.

An adjustment device 444 is also provided for traction splint 400. Adjustment device 444 is comprised of a distal pulley post 468, a proximal pulley post 470, a pair of openings 472 in inner member 414, and a rope 474. Proximal pulley post 470 is mounted to the inside of inner member 414, and distal pulley post 468 is mounted to the inside of inner member 402. Loops 478 and 480 of rope wrap around distal pulley post 468 and proximal pulley post 470, respectively. Openings 472 in inner member 414 allow for movement of inner member 414 relative to outer member 402 without inner member 414 contacting distal pulley post 468. A user of traction splint 400 can pull on the free end of rope to cause loops 478 and 480 of rope 474 around distal pulley post 468 and proximal pulley post 470, respectively, to tighten and pull distal pulley post 468 and proximal pulley post 470 toward one another. Fine adjustment device 444 allows for movement of inner member 414 relative to outer member 402 and provides fine adjustment of splint length $L_4$. Fine adjustment device 444 also provides mechanical advantage. That allows splint to reduce fractures without requiring great strength or exertion by the user. Rope 474 is attached to outer member distal end 404 at a rope attachment point 481. Once a desired splint length $L_4$ is achieved, free end of rope can be secured at a cleat 482. Fine adjustment device 444 allows inner member 414 to be moved relative to outer member 402 and allows fine adjustment of splint length $L_4$.

The adjustment device of the traction splint provides mechanical advantage. Mechanical advantage allows the splint to reduce fractures or dislocations without great strength or exertion by the user. The rope locking point is shown along the inner member distal end, but other locations on or in the splint may be utilized. The rope locking point may be comprised of a hook, cleat, or other suitable fastener for securing the rope.

Figure 5:
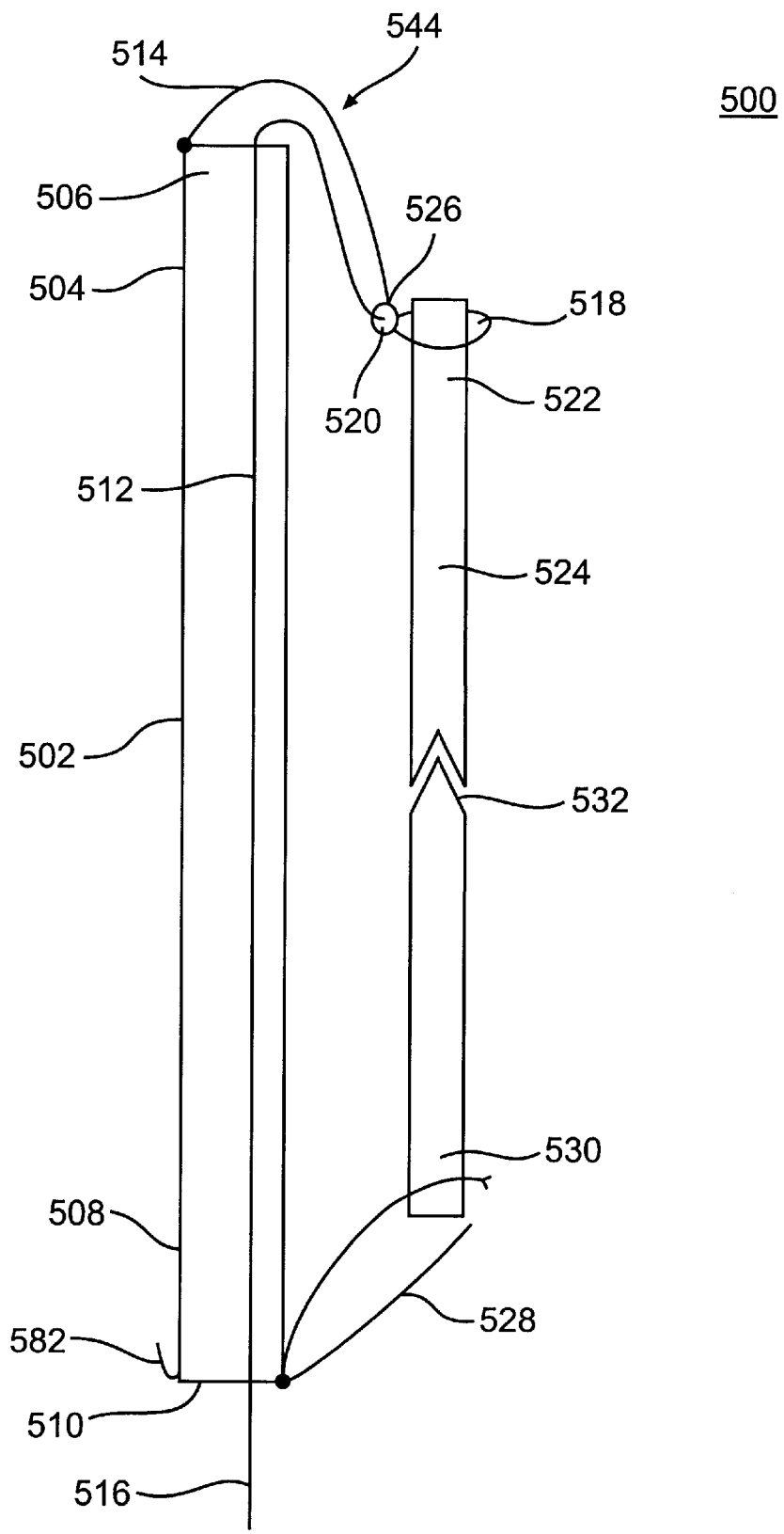
FIG. 5 is a schematic view of a fifth embodiment of a traction splint of the present invention.

FIG. 5 illustrates a fifth embodiment of the present invention. A single-member traction splint 500 includes a hollow member 502 having a member distal end 504 having an opening 506 and a member proximal end 508 having an opening 510. A rope 512 extends through hollow member 502 and includes a rope distal end 514 which extends from member distal end 504 and a free rope end 516 that extends from member proximal end 508. A constriction loop 518 is formed by forming a twist 520 at one end of rope distal end 514. Constriction loop 518 is used to secure traction splint 500 to a first end 522 of an individual's limb 524 (shown schematically for simplicity of illustration) by looping constriction loop 518 around first end 522 and using a ring connection device 526 to attach to constriction loop 518 by sliding constriction device 526 distally on rope distal end 514. A proximal securing loop 528 is attached to member proximal end 508 and is looped around a second end 530 of limb 524. By pulling on free rope end 516, first end 522 and second end 530 of limb 524 are pulled away from each other, straightening limb 524 and taking pressure off a fracture 532 in limb 524.

The distal end of the rope is preferably attached to the distal end of the member as depicted in FIG. 5, but can also be located at another location on or in the member. The rope can be fixed or removably attached to the member. The proximal securing loop is preferably attached to the proximal end of the member as shown in FIG. 5, but could be located somewhat away from the proximal end. Instead of being a piece of rope, the proximal securing loop and distal constriction loop can be made of fabric, velcro, etc.

Proximity between the member distal end and the point distal to the fracture is desirable, as well as the rope loop fitting snugly around the point distal to the fracture being secured. Although shown as a ring, the constriction device for the traction splint shown in FIG. 5 can be any suitable device that allows for rope movement. The length, relative straightness, and stability provided by the hollow member of the splint combined with a steady pull on the rope by a user contribute to a smooth straight motion of the point distal to the fracture away from the fracture, thereby reducing or securing the fracture and possibly alleviating some discomfort felt by the individual.

The hollow member shown in FIG. 5 can be circular, oval, triangular, square, rectangular, or other shape in cross-section as desired. The ratio of length to width of the hollow member can be various chosen ratios. Although the fifth embodiment of the present invention describes a hollow tube as the member, it is contemplated that a solid or otherwise not consistently hollow device could form a portion of the member. The member preferably has a hollow portion which allows the rope to pass through, but it is not necessary that the entire member be hollow. Also, the hollow portion of the member need not be of consistent diameter through the length of the tube, or centered, as shown in the embodiment of FIG. 5.

In choosing a member for the splint for a particular application, it is important to consider the number of coils of rope to be contained therein and the diameter of the rope to be employed. A suitably sized member can allow for ease of movement of the rope loops within the member but still be compact enough to be readily transportable.

Although the components in many of the embodiments of the traction splint of the present invention shown above are shown in a semi- or completely transparent state for convenience of illustration, the actual materials used to construct the structures of the present invention may or may not be translucent or transparent. Materials appropriate for construction of the outer, middle, and inner members include: metal, preferably light yet strong metals such as aluminum or titanium, durable plastics, wood, etc.

One of the benefits of the traction splint of the present invention is its ability to be readily transportable due to size and shape. Accordingly, lighter materials are favored but the invention may still be practiced with heavier materials.

Although only a few types of adjustment devices are illustrated in the drawing figures and described above, the present invention encompasses various types of conventional adjustment devices that can be used to move two members relative to each other such as: hole-and-post-type devices, ratchet devices, spring-loaded devices, pulley devices, screw-type devices, etc.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A splint, comprising:
an outer member having a distal end and a proximal end;
a middle member slidable in a longitudinal direction within said outer member, said middle member having a distal end and a proximal end;
an inner member slidable in a longitudinal direction within said middle member, said inner member having a distal end and a proximal end;
a coarse adjustment means for adjusting a distance between said distal end of said middle member and a proximal end of said outer member by a plurality of course increments;
a fine adjustment means for adjusting a distance between said distal end of said inner member and a proximal end of said middle member by a plurality of fine increments, said fine adjustment means comprising a pulley system including:
a distal pulley post mounted inside said middle member;
a proximal pulley post mounted inside said inner member;
a cord means, said cord means being looped at least once around said distal pulley post, being looped at least once around said proximal pulley post, and having an attached end attached to said middle member and a free end extending from said splint, so that when said free end is pulled, said distal pulley post and said proximal pulley post move towards each other and said distal end of said inner member and said proximal end of said middle member move away from each other.

2. The splint of claim 1, wherein:
said coarse adjustment means is comprised of a plurality of openings in said outer member and a spring loaded plunger mounted on said middle member for releasably and selectively engaging one of said openings in said outer member.

3. The splint of claim 1, wherein said coarse adjustment means comprises:
at least two paired opposed and aligned first openings in a first member selected from the group consisting of said outer member and said middle member;
a plurality of paired opposed and aligned second openings in a second member from the group consisting of said outer member and said middle member, wherein said first member and said second member are not the same; and a post for engaging and extending through two of said paired first openings in said first member, and through two of said plurality of paired second openings in said second member for preventing longitudinal movement of said middle member relative to said outer member when said post extends through said paired first openings and said paired second openings.

4. The splint of claim 1, wherein said free end of said cord means extends from said splint through an opening in said inner member.

5. The splint of claim 1, further comprising:

a distal securing means attached to said distal end of said inner member for securing said inner member to an individual's limb; and a proximal securing means attached to said proximal end of said outer member for securing said outer member to an individual's limb.

6. The splint of claim 5, wherein said distal securing means comprises a ring and said proximal securing means comprises a ring.

7. The splint of claim 1, wherein said outer member, said middle member, and said inner member are each triangular in cross-section.

8. The splint of claim 1, wherein said outer member, said middle member, and said inner member are each rectangular in cross-section.

9. The splint of claim 1, wherein said outer member, said middle member, and said inner member are each circular in cross-section.

10. A splint, comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments, said adjustment means comprising a pulley system including:

a proximal pulley post mounted inside said inner member;

a distal pulley post mounted inside said outer member;

a cord means, said cord means being looped at least once around said distal pulley post, being looped at least once around said proximal pulley post, having an attached end attached to said outer member and a free end extending from said splint, so that when said free end is pulled, said distal pulley post and said proximal pulley post move towards each other and said distal end of said inner member and said proximal end of said outer member move away from each other.

11. The splint of claim 10, wherein said free end of said cord means extends from said splint through an opening in said inner member.

12. The splint of claim 10, further comprising:

a distal securing means attached to said distal end of said inner member for securing said inner member to an individual's limb; and a proximal securing means attached to said proximal end of said outer member for securing said outer member to an individual's limb.

13. The splint of claim 12, wherein said distal securing means comprises a ring and said proximal securing means comprises a ring.

14. The splint of claim 10, wherein said outer member and said inner member are each triangular in cross-section.

15. The splint of claim 10, wherein said outer member and said inner member are each rectangular in cross-section.

16. The splint of claim 10, wherein said outer member and said inner member are each circular in cross-section.

* * * * *